（12) United States Patent
Popescu et al.

(10) Patent No.: US 9,404,857 B2
(45) Date of Patent: Aug. 2, 2016

(54) WHITE LIGHT DIFFRACTION TOMOGRAPHY OF UNLABELED LIVE CELLS

(71) Applicant: Board of Trustees of the University of Illinois, Urbana, IL (US)

(72) Inventors: Gabriel Popescu, Champaign, IL (US); Lynford L. Goddard, Champaign, IL (US); Paul Scott Carney, Champaign, IL (US); Taewoo Kim, Urbana, IL (US); Renjie Zhou, Urbana, IL (US); Mustafa A. H. Mir, Oakland, CA (US); S. Derin Babacan, San Francisco, CA (US)

(73) Assignee: The Board of Trustees of the University of Illnois, Urbana, IL (US)

( * ) Notice: Subject to any disclaimer, the term of this patent is extended or adjusted under 35 U.S.C. 154(b) by 70 days.

(21) Appl. No.: 14/313,118

(22) Filed: Jun. 24, 2014

(65) Prior Publication Data

US 2014/0307261 A1    Oct. 16, 2014

Related U.S. Application Data

(63) Continuation-in-part of application No. 13/727,875, filed on Dec. 27, 2012, now Pat. No. 9,052,180, which
(Continued)

(51) Int. Cl.
*G02B 21/06* (2006.01)
*G01N 21/45* (2006.01)
*G01N 21/47* (2006.01)

(52) U.S. Cl.
CPC ............ *G01N 21/45* (2013.01); *G01N 21/4795* (2013.01); *G01N 21/453* (2013.01)

(58) Field of Classification Search
CPC .... G02B 21/06; G02B 21/0032; G02B 21/16; G02B 21/002; G02B 21/082
USPC ......... 359/362, 363, 368, 369, 370, 371, 372, 359/385, 386, 388; 356/450, 451, 453, 456, 356/457, 511, 517
See application file for complete search history.

(56) References Cited

U.S. PATENT DOCUMENTS 6,002,480 A    12/1999    Izatt et al. ................... 356/345
8,184,298 B2    5/2012    Popescu et al. ............. 356/450
(Continued)

OTHER PUBLICATIONS

Choi et al., "Extended depth of focus in tomographic phase microscopy using a propagation algorithm," *Opt. Lett.*, vol. 33, No. 2, pp. 171-173 (Jan. 2008).
(Continued)

*Primary Examiner* — Stephone B Allen
*Assistant Examiner* — Rahman Abdur
(74) *Attorney, Agent, or Firm* — Sunstein Kann Murphy & Timbers LLP

(57) ABSTRACT

Methods for obtaining a tomographic phase image of a specimen, either in transmission or in scatter. A specimen is illuminated by a temporally incoherent source and light collected in transmission or scattering is used to generate a scattered phase image of the specimen in multiple axial planes. The scattered field is solved for in wavevector space, and a derived instrument function is deconvolved to obtain specimen susceptibility in wavevector space. The specimen susceptibility is transformed to obtain a three-dimensional phase tomogram of the specimen.

10 Claims, 7 Drawing Sheets

Related U.S. Application Data is a continuation-in-part of application No. 13/776,232, filed on Feb. 25, 2013, now Pat. No. 8,837,045.

(60) Provisional application No. 61/582,599, filed on Jan. 3, 2012, provisional application No. 61/704,005, filed on Sep. 21, 2012.

(56) References Cited

U.S. PATENT DOCUMENTS

| | | | |
|---|---|---|---|
| 2003/0065268 A1 | 4/2003 | Chen et al. | 600/473 |
| 2006/0158660 A1 | 7/2006 | Luttge et al. | 356/511 |
| 2009/0125242 A1* | 5/2009 | Choi | G01N 21/45 702/19 |
| 2013/0088723 A1* | 4/2013 | Feldkhun | G01B 9/02082 356/498 |
| 2014/0219050 A1 | 8/2014 | Park et al. | 367/7 |

OTHER PUBLICATIONS

Cuche et al., "Digital holography for quantitative phase-contrast imaging," *Opt. Lett.*, vol. 24, No. 5, pp. 291-293 (Mar. 1999).

Ding et al., "Instantaneous spatial light interference microscopy," *Opt. Express*, vol. 18, No. 2, pp. 1569-1575 (Jan. 2010).

Halder et al., "Label-Free High-Resolution Imaging of Live Cells with Deconvolved Spatial Light Interference Microscopy," *32nd Annual International Conference of the IEEE EMBS* Buenos Aires, Argentina, pp. 3382-3385 (Aug.-Sep. 2010).

Hillmann et al., "Holoscopy—holographic optical coherence tomography," *Opt. Lett.*, vol. 36, No. 13, pp. 2390-2392 (Jul. 2011).

Ikeda et al., "Hilbert phase microscopy for investigating fast dynamics in transparent systems," *Opt. Lett.*, vol. 30, No. 10, pp. 1165-1167 (May 2005).

Bhaduri et al., "Diffraction phase microscopy with white light," *Opt. Lett.*, vol. 37, No. 6, pp. 1094-1096 (Mar. 2012).

Cheng et al., "Cell death detection by quantitative three-dimensional single-cell tomography," *Biomed. Opt. Express*, vol. 3, No. 9, pp. 2111-2120 (Aug. 2012).

McNally et al., "Three-Dimensional Imaging by Deconvolution Microscopy," *Methods*, vol. 19, pp. 373-385 (1999).

Popescu et al., "Diffraction phase microscopy for quantifying cell structure and dynamics," *Opt. Lett.*, vol. 31, No. 6, pp. 775-777 (Mar. 2006).

Popescu, "Quantitative Phase Imaging of Nanoscale Cell Structure and Dynamics," *Method Cell Biol.*, Chapter 5, vol. 90, pp. 87-115 (2008).

Wang et al., "Spatial light interference tomography (SLIT)," *Opt. Express*, vol. 19, No. 21, pp. 19907-19918 (Sep. 2011).

* cited by examiner

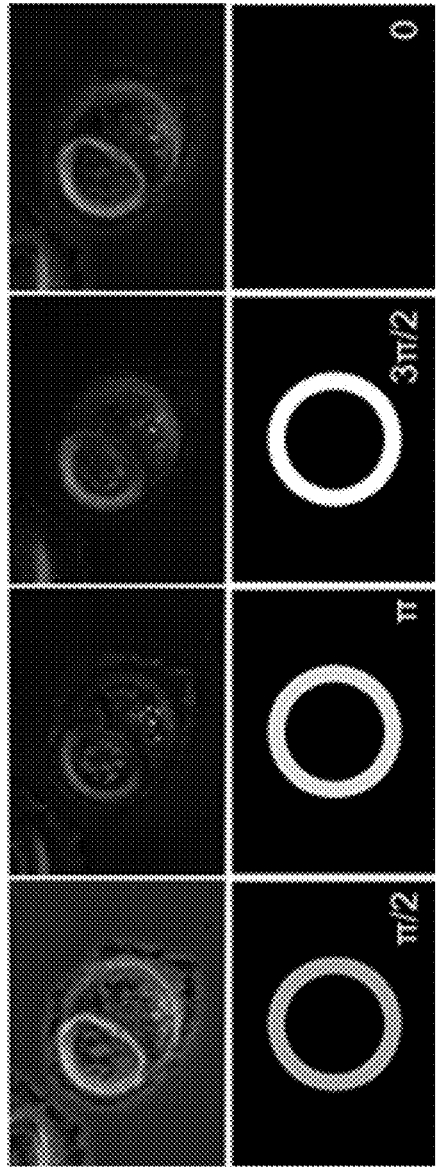
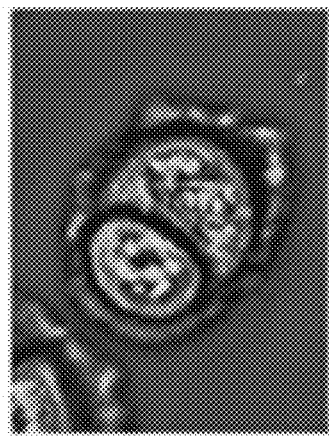
FIG. 2A  FIG. 2B  FIG. 2C  FIG. 2D
FIG. 2F  FIG. 2G  FIG. 2H  FIG. 2E
FIG. 2I

WHITE LIGHT DIFFRACTION TOMOGRAPHY OF UNLABELED LIVE CELLS

This application is a continuation-in-part of U.S. Ser. No. 13/727,875, and, through that application, claims priority from U.S. Provisional Application Ser. No. 61/582,599, filed Jan. 3, 2012.

This application is also a continuation-in-part of U.S. Ser. No. 13/776,232, filed Feb. 25, 2013, and, through that application, claims priority from U.S. Provisional Patent Application Ser. No. 61/704,005, filed Sep. 21, 2012.

All of the aforesaid US patent applications are incorporated herein by reference.

This invention was made with government support under Grants CBET0846660, CBET0939511, and CBET1040462, all awarded by the National Science Foundation. The Government has certain rights in the invention.

TECHNICAL FIELD

The present invention relates to methods of quantitative phase imaging, and, more particularly, to tomographic imaging using white light illumination of substantially transparent specimens.

DEFINITIONS

Objectives and techniques of quantitative phase imaging (QPI) are described in detail in Popescu, *Quantitative Phase Imaging of Cells and Tissues*, (McGraw-Hill, 2011), incorporated herein by reference. In QPI, the optical path length associated with substantially transparent specimens is measured and mapped, and translated into biomedically relevant information.

Off-axis phase imaging methods have provided the fastest acquisition rates by virtue of the fact that phase information, and thus optical path lengths, are extracted from a single recorded interferogram, as described, for example in Ikeda et al., *Hilbert phase microscopy for investigating fast dynamics in transparent systems*, Opt. Lett., vol. 30, pp. 1165-67 (2005), incorporated herein by reference. While diffraction-limited transverse resolution is intrinsically preserved in phase shifting methods, off-axis techniques may degrade transverse resolution. The highest temporal phase sensitivity (that is, the smallest frame-to-frame phase shift) is provided by common-path methods because they are the most stable. Finally, the highest spatial phase sensitivity (i.e., the smallest point-to-point phase change within the same frame) is obtained in the absence of speckles, which implies an incoherence in at least some respect—of the source of illumination.

Diffraction phase microscopy (DPM), as described in Popescu et al., *Diffraction phase microscopy for quantifying cell structure and dynamics*, Opt. Lett., vol. 31, pp. 775-77 (2006), incorporated herein by reference, is both off-axis and common-path, and thus combines the benefits of fast acquisition rates and high temporal sensitivity. These features enabled DPM to perform unprecedented biological studies, especially related to red blood cell membrane dynamics. Diffraction phase microscopy with white light is the subject of US Published Patent Application US 2014/0085715, which is incorporated herein by reference.

Spatial light interference microscopy (SLIM), described, for example, in U.S. Pat. No. 8,184,298 (hereinafter, "Popescu '298"), entitled "Spatial Light Interference Microscopy," and by Wang et al., *Spatial Light Interference Microscopy* (SLIM), Opt. Exp., vol. 19, pp. 1016-26 (2011), both of which are incorporated herein by reference, combines Zernike's phase contrast microscopy and Gabor's holography, has been shown to be of great value in measuring nanoscale structures and dynamics in live cells by generating endogenous contrast and mapping quantitative optical path-lengths at each point in the image.

SUMMARY OF EMBODIMENTS OF THE INVENTION

In accordance with embodiments of the invention, methods are provided for obtaining a tomographic phase image of a substantially transparent specimen. The methods have steps of:
a. illuminating the specimen with substantially temporally incoherent light through an objective of high-numerical aperture, the temporally incoherent light characterized by a focus;
b. stepping the focus of the temporally incoherent light to a sequence of successive focal planes within the substantially transparent specimen;
c. forming a scattered phase image of the specimen in an image plane where the scattered phase image of the specimen corresponds to each of the successive focal planes;
d. solving for the scattered field in wavevector space;
e. deconvolving a derived instrument function to obtain specimen susceptibility in wavevector space; and
f. transforming the specimen susceptibility to derive a three-dimensional phase tomogram of the specimen.

In accordance with alternate embodiments of the invention, the specimen may be substantially transparent in a visible portion of the electromagnetic spectrum, or, alternatively, the specimen may be opaque in the visible portion of the electromagnetic spectrum. The specimen may be substantially transparent in an infrared portion of the electromagnetic spectrum. More particularly, the specimen may be a biological cell.

In accordance with further embodiments of the present invention, forming a scattered phase image of the specimen in an image plane may correspond to measuring a temporal cross-correlation function between a scattered field and a reference plane wave, which, more particularly, may traverse the specimen.

In accordance with yet further embodiments of the present invention, forming a scattered phase image may include combining a plurality of interferograms obtained with distinct phase retardation rings. Forming a phase image may include obtaining a single interferogram from an off-axis type interferometer, such as a diffraction phase microscopy, in particular.

BRIEF DESCRIPTION OF THE DRAWINGS

The foregoing features of the invention will be more readily understood by reference to the following detailed description, taken with reference to the accompanying drawings, in which:

FIGS. 2A-2D show interferograms obtained with corresponding rings of phase retardation in FIGS. 2E-2H, processed, in accordance with SLIM, to obtain the phase image shown in FIG. 2I.

FIG. 3B is a three-dimensional rendering of an instrument transfer function using a WDT calculation in accordance with an embodiment of the present invention, while FIG. 3C is a cross-sectional slice at the $k_y=0$ plane;

DETAILED DESCRIPTION OF EMBODIMENTS OF THE INVENTION

Figure 1:
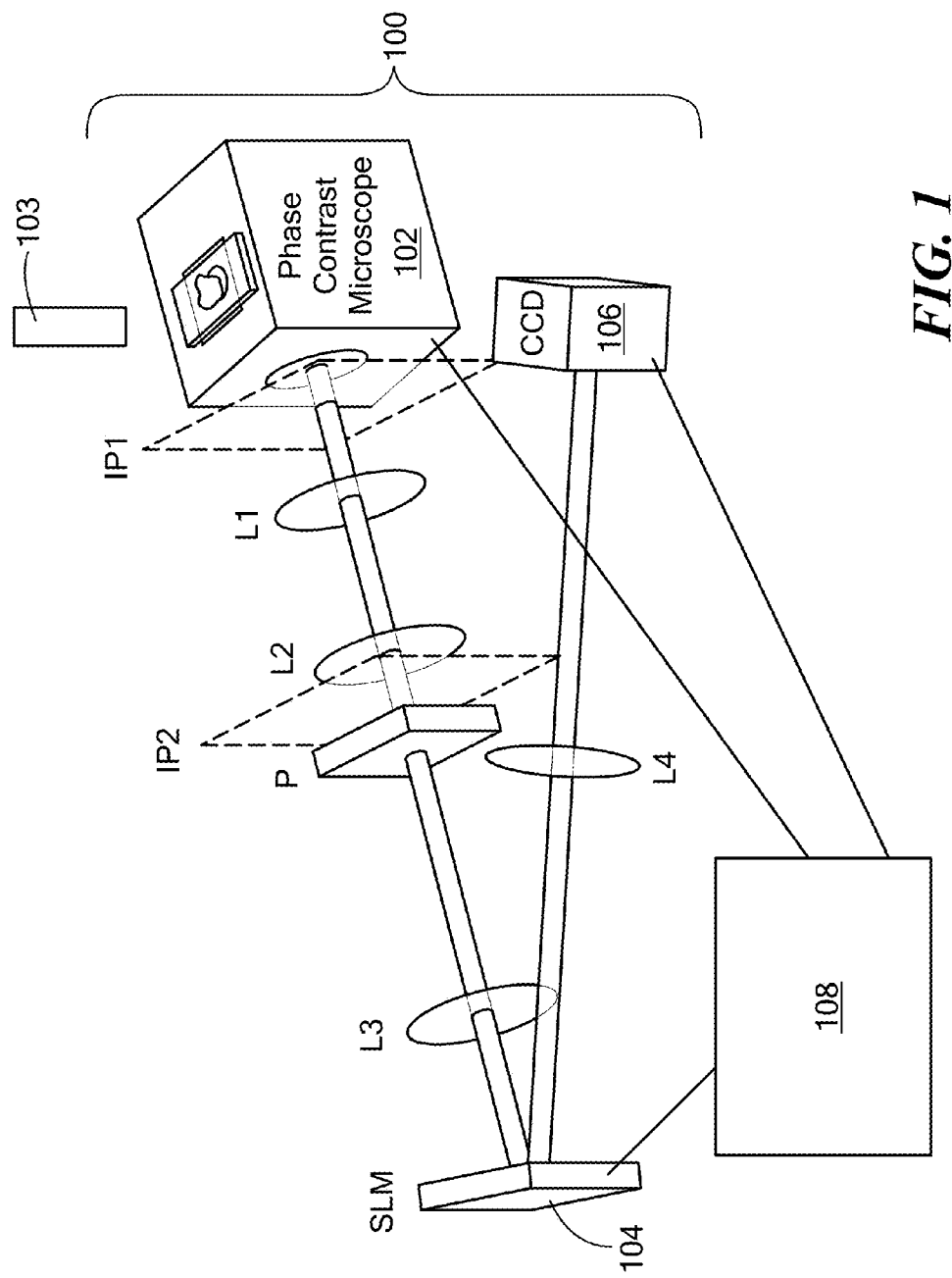
FIG. 1 is a general schematic depiction of a SLIM module used to perform a tomographic phase measurement in accordance with an embodiment of the present invention.

Further details regarding the invention described herein may be obtained by reference to Kim et al., *White-light diffraction tomography of unlabeled live cells*, Nature Photonics, DOI: 10.1038/NPHOTON.2013.350 (Jan. 19, 2014) (hereinafter, "Kim (2014)"), and in the Supplementary Information appended thereto, both of which are incorporated herein by reference.

DEFINITIONS

The term "image" shall refer to any multidimensional representation, whether in tangible or otherwise perceptible form, or otherwise, whereby a value of some characteristic (amplitude, phase, etc.) is associated with each of a plurality of locations corresponding to dimensional coordinates of an object in physical space, though not necessarily mapped one-to-one thereonto. Thus, for example, the graphic display of the spatial distribution of some field, either scalar or vectorial, such as brightness or color, constitutes an image. So, also, does an array of numbers, such as a 3D holographic dataset, in a computer memory or holographic medium. Similarly, "imaging" refers to the rendering of a stated physical characteristic in terms of one or more images.

As used herein, "label-free" refers to a method of imaging a substantially transparent sample that does not require introduction of materials, such as fluorophores or contrast agents that are extrinsic to the imaged sample.

The terms "object," "sample," and "specimen" shall refer, interchangeably, to a tangible, non-transitory physical object capable of being rendered as an image.

The term "temporally incoherent" as applied to a source of irradiation shall refer to a source characterized by a coherence time $\tau_c$ that is no longer than 10 cycles of a central frequency of the light emitted by the source.

The term "substantially high spatial coherence" as applied to a beam of light shall denote a condition of coherence wherein if two slits were to be placed within the a coherence area exceeding the field of view in a plane transverse to the beam propagation axis, at least one interference null would result in the far field where the intensity is no greater than 10% of the peak intensity of the beam.

"High numerical aperture," for purposes of the present description and claims, shall refer to NA>0.5, which for visible light insures a transverse resolution better than one micron.

Comment Regarding Notation:

For convenience of notation in the current description, the same symbol is used for a function and for its Fourier transform. In order to indicate the domain in which the function operates, all the arguments are carried explicitly, e.g., $f(k_\perp,z;\omega)$ is the Fourier transform of $f(r_\perp, z; t)$ over $r_\perp$ and t.

Embodiments of the present invention, significantly, measure a complex field at an image plane. Complex field measurements in an image plane have been shown, as in Ding et al., *Fourier transform light scattering of inhomogeneous and dynamic structures*, Phys. Rev. Lett., vol. 101, 238102 (2008), incorporated herein by reference, to yield higher sensitivity than scatter measurements in the far zone. Once a complex field has been measured at successive depths to form a z-stack of complex images, the complex field stack is processed using white light diffraction tomography (WDT) in accordance with the following teachings of the present invention.

FIG. 1 shows a schematic of a SLIM module 100, designed as an add-on module to a commercial phase contrast microscope 102 (otherwise referred to herein as the "microscope"), such as an Axio Observer Z1, which may be obtained from Carl Zeiss Microscopy, LLC. The back focal plane of the objective lens (not shown) contains a thin metal annulus (the "phase ring") which provides a π/2 phase shift between the scattered and unscattered light. In one embodiment of a SLIM system, the image plane of the phase contrast microscope 102 is first relayed and magnified through a 4f system formed by two focusing lenses, L1 and L2. The back focal plane of the objective lens is imaged onto a spatial light modulator (SLM) 104, such as a programmable liquid crystal spatial light modulator that may be obtained from Boulder Nonlinear Systems, Inc., Boulder, Colo., which is located in the Fourier plane of a second 4f system formed by L3 and L4. A desired ring pattern is projected onto the SLM, and is matched to the image of the phase ring on the SLM. In this manner the SLM is used to provide additional phase shifts of 0, π/2, π and 3π/2 (shown in FIGS. 2E-2H) between the scattered and un-scattered light. Thus, four phase shifted interferograms, shown in FIGS. 2A-2D, are recorded at the image plane (at the focus of the second Fourier lens L4) using a CCD detector 104. The SLM 104, CCD 106, and microscope 102 are synchronized through a processor 108 executing a software program. In a typical implementation, 8 frames are acquired per second, corresponding to 2 quantitative phase images (QPI) per second, although it is to be understood that other data acquisition rates may be practiced within the scope of the present invention. The acquisition rate is typically limited by the frame rate of the CCD and the refresh rate of SLM. At the rate discussed here by way of example, a z-stack of 100 slices can be obtained in 50 seconds. By using these four interferograms, the actual phase shift (shown in FIG. 2I) caused by the sample can be uniquely determined within a range of 2π. Any 2π ambiguities are corrected by Goldstein's unwrapping algorithm, which is described in Goldstein et al., *Satellite radar interferometry: Two-dimensional phase unwrapping*, Radio Science, vol. 23, pp. 713-20 (1988), which is incorporated herein by reference. Determination of the phase φ(r, t) of the imaged object based on the four phase-shifted interferograms is described, for example, in Popescu '298.

A sample (not shown) is transilluminated, in microscope 102, by a broadband source 103. In one example, the broadband source is a halogen lamp with a temporal coherence length of 1.2 μm. The broadband source 103 (also referred to, herein, as a "lamp") assumes a significant role in increasing resolution since it does not suffer from speckle, and thus, improves the sensitivity.

Insofar as the SLIM module 100 is preferably an add-on module to a commercial microscope, it is possible to overlay SLIM with other microscopy modalities (e.g. epi-fluorescence, or DIC), within the scope of the present invention. In particular, within the scope of the present invention, a phase image may be obtained from a single interferogram from an off-axis type interferometer, such as a diffraction phase microscope, for example.

With these features, SLIM is capable of performing multimodal and functional studies. Furthermore, with the short coherence length and a high numerical aperture objective, SLIM may advantageously provide excellent depth sectioning (1.2 µm depth sectioning for a 63×/1.4 NA objective), which plays a large role in the reconstruction method described herein.

Figure 3A:
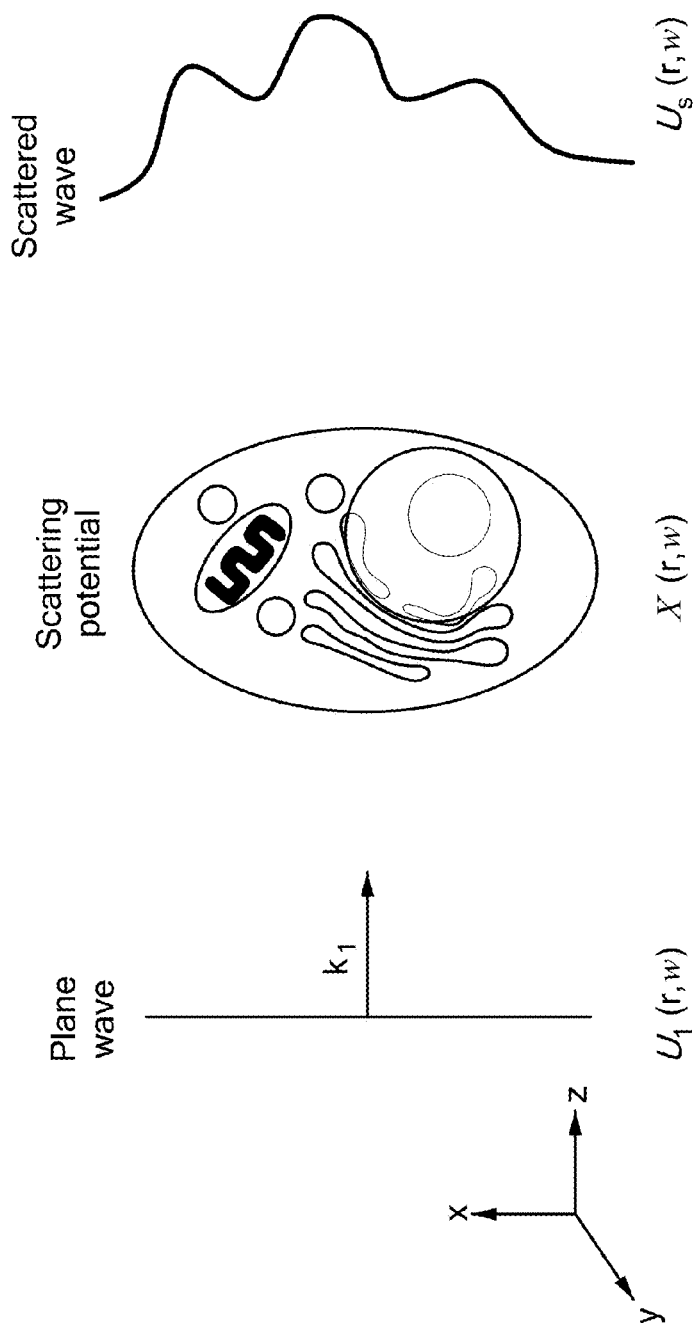
FIG. 3A depicts light scattering by a scattering potential under the first-order Born approximation.

It is known that the Rytov approximation is more appropriate for reconstructing smooth objects with respect to the wavelength of light, i.e., for low-resolution imaging, while the Born approximation works better for imaging finer structures. Thus, for purposes of resolving features of imaged cells, for example, the latter is appropriate, and is used for purposes of the discussion herein. Under the first-order Born approximation, illustrated in FIG. 3A, with an incident plane wave, $U_i = A(\omega)e^{i\beta(\omega)z}$, the forward scattered field $U_s$ is solved in the wavevector space, as described above, instead of using the traditional Green's function and Weyl's formula approach.

For purposes of the present teachings, a temporal cross-correlation function, $\Gamma_{12}(r,\tau)$, is usefully defined as follows:

$$\Gamma_{12}(r,\tau) = \langle U_s(r,t)U_r^*(r,t+\tau) \rangle, \quad (1)$$

where $U_s$ and $U_r$ are the scattered and the reference (unscattered) field, respectively. $\Gamma_{12}(r,\tau)$ is a complex function that can be written as $$\Gamma_{12}(r,\tau) = |\Gamma_{12}(r,\tau)|e^{i\phi(r,\tau)}, \quad (2)$$

where $\phi(r,\tau)$ is the phase associated with the image field, measured in SLIM using the four phase shifted interferograms, as discussed above. The generalized Wiener-Khintchine theorem (see Wiener, *Generalized harmonic analysis*, *Acta Mathematica*, vol. 55, pp. 117-258 (1930), incorporated herein by reference) allows $\Gamma_{12}(r,\tau)$ to be related to the cross-spectral density through Fourier transform of $$\Gamma_{12}(r,\tau) = \int_0^\infty W_{12}(r,\omega)e^{i\omega\tau}d\omega \quad (3)$$

where, $$W_{12}(r,\omega) = \langle U_s(r,\omega)U_r^*(r,\omega) \rangle. \quad (4)$$

During the phase shifting measurement, $\Gamma_{12}(r,\tau)$ is evaluated at $\tau=0$, to yield:

$$\Gamma_{12}(r,\tau=0) = \int_0^\infty \langle U_s(r,\omega)U_r^*(r,\omega) \rangle d\omega, \quad (5)$$

in which the unknown quantity is the scattered field, $U_s$. In the following, an analytical solution is derived for $U_s$ which establishes the relationship between the measurable quantity, $\Gamma_{12}$, and the 3D object structure of interest.

The inhomogeneous Helmholtz equation, which describes the field U in a medium with index distribution of n(r) is $$\nabla^2 U(r,\omega) + n^2(r,\omega)\beta_0^2(\omega)U(r,\omega) = 0, \quad (6)$$

where $\beta_0(\omega) = \omega/c$ is the wavenumber in vacuum. Eq. (6) may be rearranged as $$\nabla^2 U(r,\omega) + \beta^2(\omega)U(r,\omega) = -\chi(r,\omega)\beta_o^2(\omega)U(r,\omega), \quad (7)$$

where $\beta(\omega) = \bar{n}\beta_0(\omega)$ (we assume non-dispersive objects), $\bar{n} = \langle n(r) \rangle_r$ is the spatially averaged refractive index, and $\chi(r,\omega) = n^2(r,\omega) - \bar{n}^2(\omega)$ is the scattering potential. The total field $U(r,\omega)$ can be written as $U(r,\omega) = U_i(r,\omega) + U_s(r,\omega)$, where $U_i(r,\omega)$ is the incident wave. $U_i$ satisfies the homogeneous wave equation, $$\nabla^2 U_i(r,\omega) + \beta^2(\omega)U_i(r,\omega) = 0. \quad (8)$$

Eq. (8) has a plane-wave solution $U_i(r,\omega) = A(\omega)e^{i\beta(\omega)z}$ where $A(\omega)$ is the spectral amplitude of the incident field. Subtracting Eq. (7) from Eq. (8) gives $$\nabla^2 U_s(r,\omega) + \beta^2(\omega)U_s(r,\omega) = -\chi(r)\beta_o^2(\omega)U(r,\omega). \quad (9)$$

Eq. (9) makes clear that the driving term of the right hand side represents the interaction of the object scattering potential $\chi$ with the total field U. Under the first Born approximation, i.e., $|U_s(r,\omega)| \ll |U_i(r,\omega)|$, $U(r,\omega)$ on the right hand side can be approximated as $U_i(r,\omega)$, allowing Eq. (9) to be re-written as, $$\nabla^2 U_s(r,\omega) + \beta^2(\omega)U_s(r,\omega) = -\chi(r,\omega)\beta_o^2(\omega)A(\omega)e^{i\beta(\omega)z}. \quad (10)$$

Instead of employing the traditional Green's function approach and the angular spectrum representation (Weyl's formula), the scattered field directly may be solved for directly in wavevector space, using the 3D Fourier transformation. First, a 3D Fourier transform of Eq. (10) is performed, which yields $$[\beta^2(\omega) - k^2]U_s(k,\omega) = -\beta_0^2(\omega)A(\omega)\chi[k_\perp, k_z - \beta(\omega)]. \quad (11)$$

In Eq. (11), we used the shift theorem of Fourier transforms, namely, $\chi(r,\omega)e^{i\beta(\omega)z} \to \chi[k_\perp, k_z - \beta(\omega)]$, where the arrow indicates Fourier transformation. Note that, throughout the manuscript, we use the same symbol for a function and its Fourier transform but carry all the arguments explicitly, which clearly identifies the domain in which the function operates. For example, $\chi(k)$ is the Fourier transform of $\chi(r)$. From Eq. (1), the scattered field $U_s$ s obtained immediately as $$U_s(k, \omega) = -\beta_0^2(\omega)A(\omega)\frac{\chi[k_\perp, k_z - \beta(\omega)]}{\beta^2(\omega) - k_\perp^2 - k_z^2}. \quad (12)$$

Next, an expression is derived for the field as a function of axial distance z, i.e., we arrange the terms such that a 1D inverse Fourier transform with respect to $k_z$ can be easily performed. Toward this end, a $k_\perp$-dependent propagation constant is defined, $q = \sqrt{\beta^2(\omega) - k_\perp^2}$, Eq. (12) is rewritten as $$U_s(k, \omega) = -\beta_0^2(\omega)A(\omega)\chi[k_\perp, k_z - \beta(\omega)]\frac{1}{2q}\left(\frac{1}{k_z - q} - \frac{1}{k_z + q}\right). \quad (13)$$

In instances where the transmitted or forward-scattered field is acquired, the backscattered field (the second term in the right-most parentheses) may be ignored. Conversely, if the backscattered field is exclusively acquired, the forward scattering term may be ignored. However, implementation of the methods of the present invention to encompass the backscattered field is similarly within the capability of a person of ordinary skill in the art, once the present teachings have been appreciated. Solely for heuristic purposes, the teachings that follow will be expressed in terms of a forward scattered field, though their application to backscattered fields is within the scope of the present invention.

Performing an inverse Fourier transform on Eq. (13) with respect to $k_z$ in order to obtain the forward-scattered field (for example) as a function of transverse wavevector, $k_\perp$, axial distance, z, and angular frequency, $\omega$, one obtains:

$$U_s(k_\perp, z; \omega) = -\frac{\beta_0^2(\omega)A(\omega)}{2q}[\chi(k_\perp, z)e^{i\beta(\omega)z}]\circledvee_z e^{iqz} \quad (14)$$

In Eq. (14), $\circledvee_z$ indicates convolution along the z-dimension, $$f(z)\circledvee_z e^{iqz} = \int_{-\infty}^{\infty} f(z')e^{iq(z-z')}dz'.$$

can be easily seen that the convolution of a function with a complex exponential yields the Fourier transform of that function multiplied the complex exponential, which yields the simple result $[\chi(k_\perp, z; \omega)e^{i\beta(\omega)z}]\circledvee_z e^{iqz} = e^{iqz}\chi[k_\perp, q-\beta(\omega)]$.

In order to insert the result of Eq. (14) into Eq. (3), $\Gamma_{12}(r,\tau)$ is Fourier transformed with respect to the transverse position vector, $r_\perp = (x,y)$. Since $U_r(r,\omega)$ is a plane wave propagating in z-direction, Eq. (a4) in $k_\perp$-space is $$W_{12}(k_\perp,z,\omega) = \langle U_s(k_\perp,z,\omega)U_r^*(z,\omega)\rangle. \quad (15)$$

Using the solution of $U_s$ from Eq. (b9) and $U_r(z,\omega) = A(\omega)e^{i\beta(\omega)z}$, one has $$W_{12}(k_\perp, z, \omega) = \frac{-\beta_o^2(\omega)S(\omega)e^{iz[q-\beta(\omega)]}}{2q}\chi[k_\perp, q-\beta(\omega)], \quad (16)$$

where $S(\omega) = |A(\omega)|^2$ is the power spectrum of the illumination field. Using Eq. (3), one obtains the temporal cross correlation at zero-delay as a function of the frequency integral $$\Gamma_{12}(k_\perp, z, 0) = -\int_0^\infty \frac{\beta_o^2(\omega)S(\omega)e^{iz[q-\beta(\omega)]}}{2q}\chi[k_\perp, q-\beta(\omega)]d\omega. \quad (17)$$

With the relation $\beta(\omega) = \bar{n}\beta_0 = \bar{n}\omega/c$, the integral from $d\omega$ to $d\beta$, $S(\omega)$ can be changed to $S(\beta c/\bar{n})$, such that Eq. (17) becomes $$\Gamma_{12}(k_\perp, z, 0) = -\frac{c}{2\bar{n}^3}\int_0^\infty \frac{\beta^2 S(\beta c/\bar{n})e^{iz(q-\beta)}}{q}\chi(k_\perp, q-\beta)d\beta. \quad (18)$$

In practicing the present invention, what is measured is $S(\lambda)$. So, to obtain the spectrum distribution for $S(\beta c/\bar{n})$ from $S(\lambda)$, one considers the Jacobian transformations, $S(\beta c/\bar{n}) \leftrightarrow \bar{n}S(\beta)/c$ and $S(\beta) \leftrightarrow \lambda^2 S(\lambda)/2\pi$. In order to evaluate the integral in Eq. (18), a new variable $Q = q - \beta = \sqrt{\beta^2 - k_\perp^2} - \beta$ is defined, from which are derived $$\beta = -\frac{Q^2 + k_\perp^2}{2Q}$$

and $$q = \left(-\frac{Q}{2} + \frac{k_\perp^2}{2Q}\right).$$

Substituting $d\beta$ for $dQ$, the Jacobian becomes $$\frac{d\beta}{dQ} = \left(-\frac{1}{2} + \frac{k_\perp^2}{2Q^2}\right),$$

and Eq. (18) becomes:

$$\Gamma_{12}(k_\perp, z; 0) = \frac{1}{8\bar{n}^2}\int_0^\infty \frac{(Q^2+k_\perp^2)^2}{Q^3}S\left(-\frac{Q^2+k_\perp^2}{2Q}\right)\chi(k_\perp, Q)e^{izQ}dQ \quad (19)$$

$$= \frac{1}{8\bar{n}^2}FT_Q^{-1}\left[\frac{(Q^2+k_\perp^2)^2}{Q^3}S\left(-\frac{Q^2+k_\perp^2}{2Q}\right)\right]\circledvee_z\chi(k_\perp, -z)$$

$$= \Sigma(k_\perp, -z)\circledvee_z\chi(k_\perp, -z).$$

In Eq. (19), $\Sigma$ is the function that incorporates all the details of the instrument response. Note that the $k_\perp$ coverage of $\Sigma$ is limited to a maximum value $k_\perp^{max} = \beta_0 NA$, where NA is the numerical aperture of the objective. By measuring z-stacks in SLIM, it becomes possible to reconstruct the object's 3D distribution through deconvolution of Eq. (19). Alternatively, Eq. (19) may be written in the spatial frequency domain as a product, namely, $$\Gamma_{12}(k_\perp, Q; 0) = \Sigma(k_\perp, Q)\chi(k_\perp, Q), \quad (20)$$

where, $$\Sigma(k_\perp, Q) = \frac{1}{8\bar{n}^2}\frac{(Q^2+k_\perp^2)^2}{Q^3}S\left(-\frac{Q^2+k_\perp^2}{2Q}\right). \quad (21)$$

Calculating the Point Spread Function (PSF)

Since Eq. (21) gives the coherent transfer function, i.e., the Fourier transform of the point spread function (PSF) of the imaging system, therefore, by measuring the source spectrum and filtering according to the NA of the objective, the coherent transfer function of the system can be calculated directly. The PSF of the imaging system may also be referred to herein equivalently as an "instrument function."

First, the optical spectrum of the lamp 103 is measured at a specified temperature, such as 3200K, using a fiber optic spectrometer, for example. Insofar as the spectrum SW is measured as in air, we perform the Jacobian transformation introduced in the previous section to obtain the spectrum in terms of the variable $\beta = -(Q^2 + k_\perp^2)/2Q$. Next through numerical calculations, this spectrum is resampled onto a 3D grid in spatial-frequency space ($k_x$, $k_y$, Q). For a 63×/1.4 NA objective, each pixel in space corresponds to 45 nm and each z-slice is separated by 200 nm. Because of the quadratic relationship between Q and $\beta$, the resampling yields two duplicates of the spectrum. Therefore, the second of the two duplicates which appears at high Q is removed by applying a spatial low-pass filter with cutoff $Q = k_\perp$. Further filtering in Q is performed to incorporate the physical minimum and maximum value of Q and the maximum value, which is determined by the NA of the objective, $k_\perp^{max} = \beta_0 NA$. In order to avoid well known numerical artifacts due to sharp cutoffs in the frequency domain, we used a simple apodization procedure to smooth the edges of the filter function. The filter function may be convolved with a narrow Gaussian function, of a width that is 5% of the system's maximum transverse frequency. Finally, the coherent transfer function is Fourier transformed to obtain the PSF. The complex PSF is then used for the 3D reconstruction, as detailed below.

Deconvolution

As discussed above, SLIM measures the 3D complex field distribution, i.e. phase and amplitude, which can be expressed as a convolution between the point spread function (PSF) of the imaging system, $\Sigma(r)$, and the structure of the object, $\chi(r) = n^2(r) - \bar{n}^2$. The real field may be represented as a complex analytic signal, $\overline{U}(r) = \chi(r) \circledv \Sigma(r) + \zeta(r)$, which also contains a signal independent noise term, $\zeta(r)$. Considering a weakly scattering phase object with very small absorption, where most of the useful information is contained in the phase image, it is reasonable to assume that the amplitude of the field is constant over the entire space. Therefore, the deconvolution can be performed on the phase term only, $\exp[i\Phi(r)]$.

The function that is minimized, in accordance with a preferred embodiment of the invention, is $$\hat{\Phi}(r) = \underset{\Phi(r)}{\mathrm{argmin}} \frac{1}{2\sigma^2} \|\exp[i\overline{\Phi}(r)] - \Sigma(r)\circledv\exp[i\Phi(r)]\|^2 + \rho R[\Phi(r)] \quad (22)$$

where $\sigma^2$ is the noise variance, $\rho$ is the regularization parameter, and R is the regularization functional. For simplification, these purely phase-dependent fields can be expressed in vector forms:

$$\hat{f} = \underset{f}{\mathrm{argmin}} \frac{1}{2\sigma^2} \|g - \Sigma f\|^2 + \rho R(f) \quad (23)$$

where g represents the measured field, $\exp[i\overline{\Phi}(r)]$, f represents the unknown field from the structure, $\exp[i\Phi(r)]$, and $\Sigma$ represents the convolution matrix corresponding to the PSF.

Phase contrast (PC) images are highly sensitive to the sharp object boundaries, but not to slow variations in the background region. For small scale objects, such as a biological cell, these characteristics of PC permit the use the sparse representation, described, for example, in Shechtman et al., *Sparsity-based sub-wavelength imaging with partially incoherent light via quadratic compressed sensing*, Opt. Express, vol. 19, pp. 14807-22 (2011), incorporated herein by reference. When an appropriate transform is applied to a phase image, only a few of the transform coefficients contain most of the signal energy while all the other coefficients become very small. This situation is known as transform sparsity. In a preferred embodiment of the present invention, the first- and second-order directional difference operators, [−1 1] and [−1 2 −1], along with 45° and −45° first-order derivative filters, $$\begin{bmatrix} -1 & 0 \\ 0 & 1 \end{bmatrix} \text{ and } \begin{bmatrix} 0 & -1 \\ 1 & 0 \end{bmatrix},$$

are used as transforms. For each plane in the image, x-y, y-z and z-x, these 2D transforms are applied and total of 12 transforms are generated to hold the spatial variations. Therefore, by applying the sparse deconvolution principle with these filters, the problem in Eq. (23) can be expressed as $$\hat{f}, \hat{\alpha}_{ki} = \underset{f, \alpha_{ki}}{\mathrm{argmin}} \frac{1}{\sigma^2} \|g - \Sigma f\|^2 + \sum_k (D_k f)^T A_k (D_k f) \quad (24)$$

where $\alpha_{ki}$ are the weighting coefficients for each plane, i, $D_k$ are the transform matrices, and $A_k$ are diagonal matrices with $\alpha_{ki}$ in the diagonal. This problem is solved by an alternating iterative minimization scheme where only one unknown is estimated at a time while others are fixed. As a result, the complex image f is estimated by taking derivative of Eq. (24) and setting it to zero. Therefore, the solution is of the structure is, $$\hat{f} = \left(\Sigma^T \Sigma + \sigma^2 \sum_k D_k^T A_k D_k\right)^{-1} \Sigma^T g \quad (25)$$

and the weighting coefficients are estimated to be, $$\hat{\alpha}_{ki} = \frac{1}{\left|(D_k \hat{f})\right|_i^2 + \varepsilon} \quad (26)$$

where $\varepsilon$ is a small number $10^{-9}$, in a preferred embodiment) used to avoid the trivial solution.

Application to Tomographic Reconstruction

It is known that It is known that the Rytov approximation is more appropriate for reconstructing smooth objects with respect to the wavelength of light, i.e., for low-resolution imaging, and the Born approximation works better for imaging finer structures. Thus, for purposes of resolving features of imaged cells, for example, the latter is appropriate, and is used for purposes of the discussion herein. Under the first-order Born approximation, with an incident plane wave, $U_i = A(\omega)e^{i\beta(\omega)z}$, the forward scattered field $U_s$ is solved in the wavevector space, as described above, instead of using the traditional Green's function and Weyl's formula approach. In the transverse wavevector domain, $k_\perp$, $U_s$ can be expressed, per Eq. (13), as $$U_s(k_\perp, z; \omega) = -\frac{\beta_0^2(\omega) A(\omega) e^{iqz}}{2q} \chi[k_\perp, q - \beta(\omega)], \quad (27)$$

with symbols as defined above. The dispersion in the object may be neglected, because most biological samples of interest here are weakly absorbing. This is true even for single red blood cells. Even though the haemoglobin absorbs strongly in blue, the overall absorption of visible light through a single red blood cell is very small. This is so because the absorption length of haemoglobin in a normal red blood cell is around 10 μm in blue (averaged over 400-500 nm wavelength) and around 3 mm in red (averaged over 600-750 nm wavelength), while the thickness of the cell is only 2-3 μm.

In conventional phase shifting interferometry, the cross-correlation of the scattered and reference fields is measured as $\Gamma_{12}(r_\perp, z, \tau) = \langle U_s(r_\perp, z, t) U_r^*(z, t+\tau)\rangle$ at $\tau = 0$ which is equivalent to integrating the spectrum over $\omega$. Knowledge of the spatial frequency response of our instrument, or coherent transfer function (see Supplementary Information), $\Sigma(k_x, k_y, k_z)$, allows us to write the main result of our calculation, i.e., the solution to the inverse scattering problem, in terms of the measured data, $\Gamma_{12}$, and the instrument function (or the coherent transfer function), $\Sigma$, in the wave-vector domain as, $$\chi(k) = \frac{\Gamma_{12}(k; 0)}{\Sigma(k)}. \quad (28)$$

In practice, the operation in Eq. (28) requires regularization, as discussed above. $\Sigma(k)$ is given by $$\Sigma(k) = \frac{1}{8\bar{n}^2} \frac{(Q^2 + k_\perp^2)^2}{Q^3} S\left(-\frac{Q^2 + k_\perp^2}{2Q}\right). \quad (29)$$

In Eq. (29), S is the optical spectrum of the imaging field as a function of the wavenumber and $Q = \sqrt{\beta^2 - k_\perp^2} - \beta$. The 3D point spread function can be obtained, as shown above, through an inverse Fourier transform of Eq. (29).

Figures 3B, 3C:
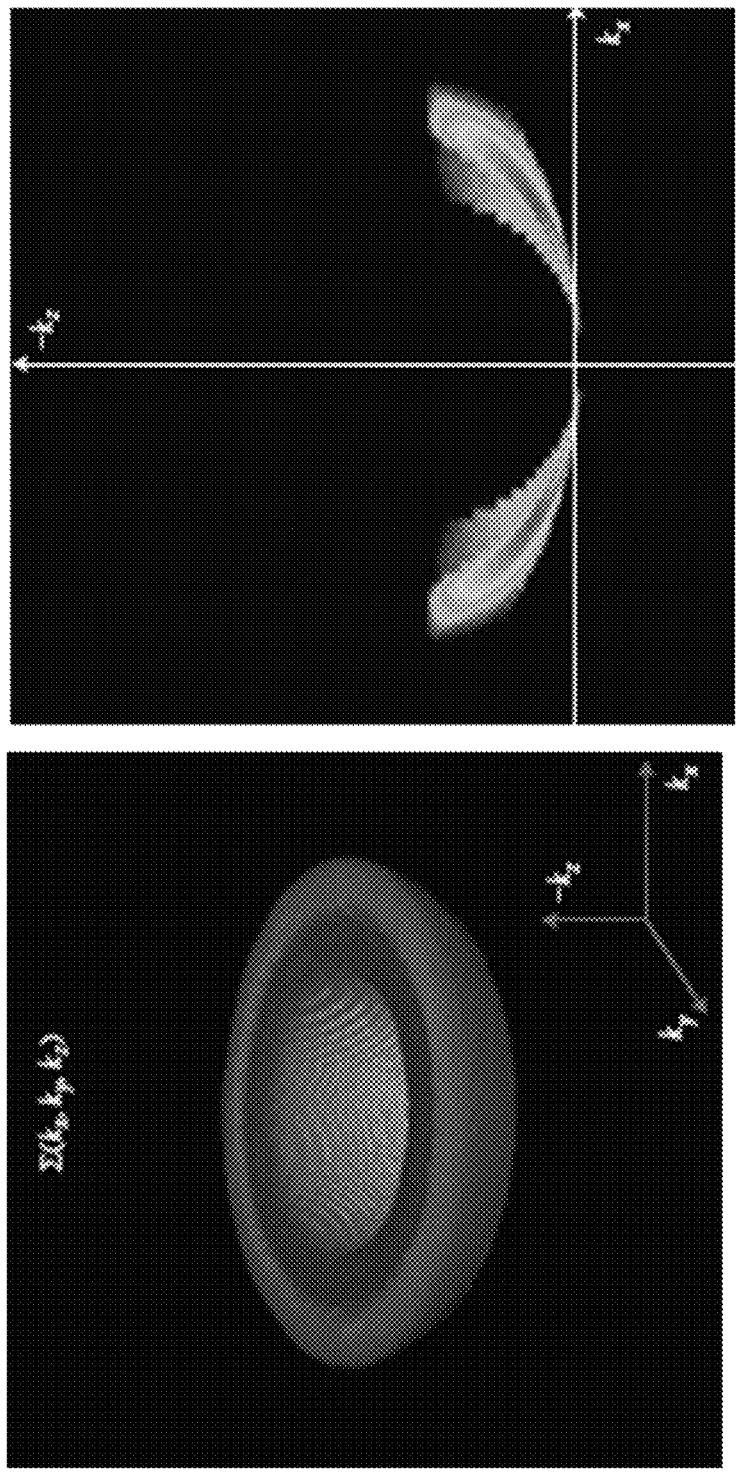

Qualitatively, $\Sigma$ has a physically intuitive behaviour, of which salient features are depicted in FIGS. 3B and 3C. Specifically, its dependence on z is related to the optical spectrum, $S(\omega)$, via a Fourier transform, meaning that a broader optical spectrum gives a narrower function, $\Sigma(z)$. This relationship explains the inherent optical sectioning capabilities of the instrument. This type of optical gating, in which axial resolution is determined by the coherence properties of the illumination light, has been successfully employed in optical coherence tomography (OCT) of deep tissues, for example. However, there are significant differences between WDT and OCT. In OCT, the cross-correlation $\Gamma_{12}$ is resolved over a broad delay range, which provides the depth dimension of the object. In WDT, the z-information is collected by scanning the object through focus.

Most importantly, in methods in accordance with the present invention, the coherence gating works in synergy with the high numerical aperture (NA) optics and, thus, allows for high resolution tomography. In other words, in WDT, coherence gating by itself would not work at zero NA and, conversely, high NA gating would not work with monochromatic light.

Figure 4:
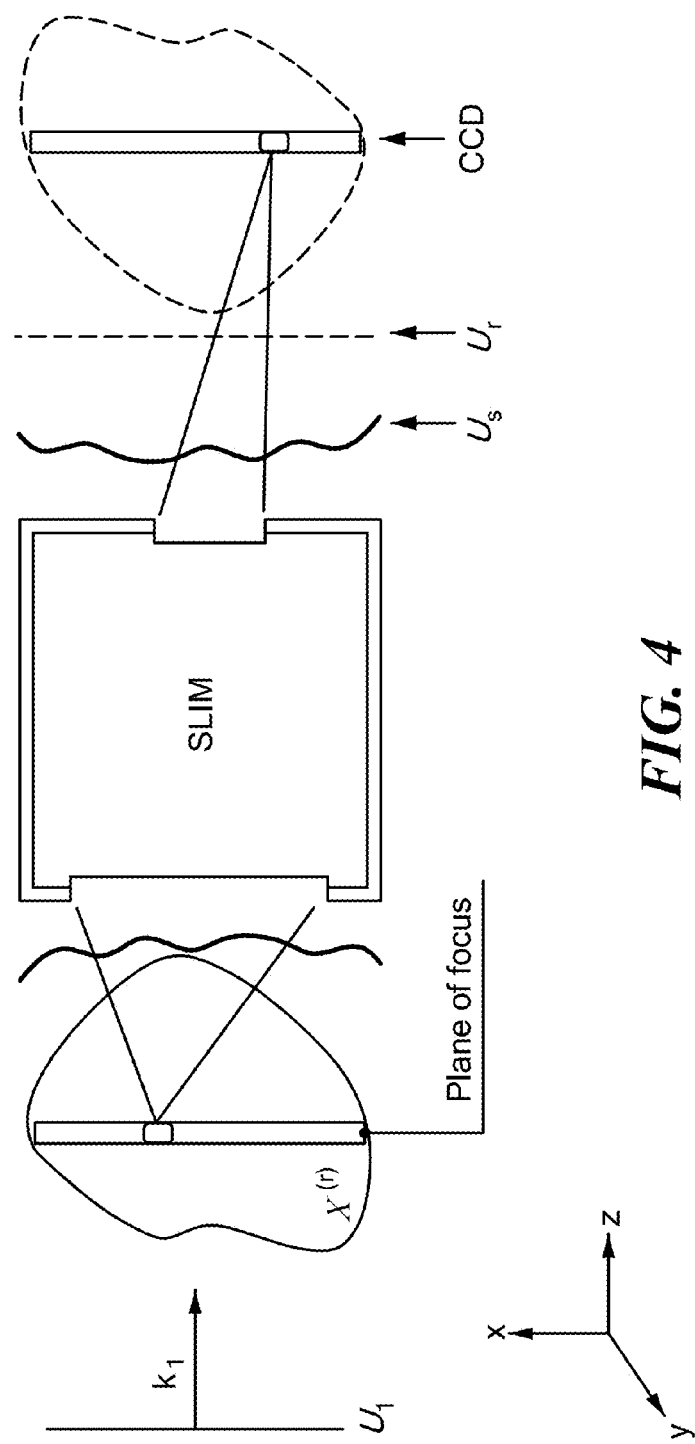
FIG. 4 is a schematic depiction of optical phase sectioning of a specimen in accordance with embodiments of the present invention.

Use of broadband light from source 103 and high numerical aperture objectives results in optical sectioning capabilities highly advantageous for high resolution tomography. The function $\Sigma(k_x, k_y, k_z)$ for an imaging system in accordance with embodiments of the present invention is illustrated in FIGS. 3B and 3C: a three-dimensional rendering in FIG. 3B, and a cross-section at the $k_y=0$ plane, in FIG. 3C. As expected, the width of the k coverage increases with $k_x$, which indicates that the sectioning is stronger for finer structures or, equivalently, higher scattering angles. The structure of the object is recovered through a sparse deconvolution algorithm, as described above. Acquisition of phase images, in each plane of a z-stack of images, proceeds in accordance with the paradigm discussed above and depicted in FIG. 4. Experimentally, $\Sigma$ was measured by imaging a microsphere much smaller than the resolution of the system, in accord with theoretical expectations.

Example I

Tomography of *Escherichia coli*

Figures 5A, 5B, 5C:
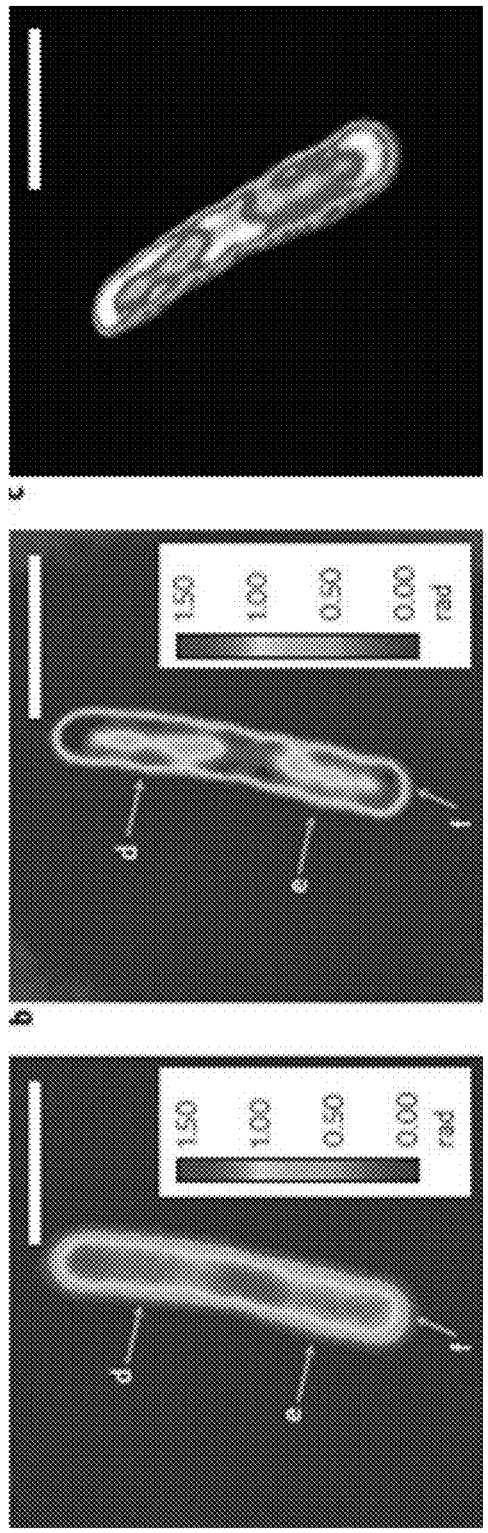
FIGS. 5A and 5B show the middle frame of a z-stack of raw data acquired in imaging an *E. coli* cell and a reconstructed z-stack, in accordance with an embodiment of the present invention. The 3D rendering of this *E. coli* cell is shown in FIG. 5C.

The approach described herein in accordance with the present invention was applied to obtain three-dimensional images of *Escherichia coli* (*E. coli*) cells. A z-stack consisting of 17 slices with a step size of 280 nm was obtained. FIGS. 5A and 5B show the middle frame of raw data and the reconstructed z-stack. Upon deconvolution, the previously invisible protein helical subcellular structure of *E. coli* is resolved. The 3D rendering of this *E. coli* cell is shown in FIG. 5C. Only the bottom half of the cell is shown in the figure to emphasize the helical subcellular structure.

WDT was also employed to obtain 3D images of speculated red blood cells, shown in Kim (2014), to which the interested reader is directed.

Example II

Tomography of HT29 Cells

Figure 6:
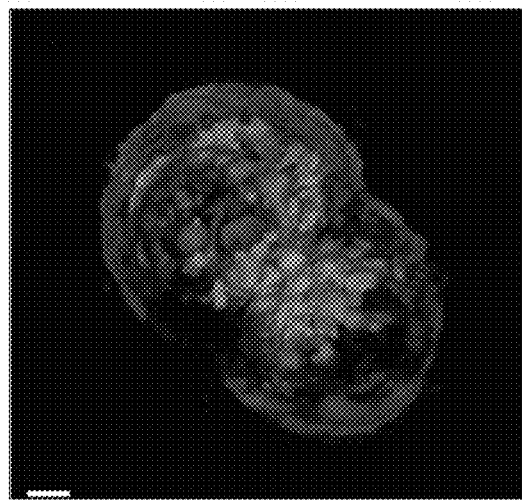
FIG. 6 shows a false-coloured 3D image of an HT-29 cell, employing WDT methods in accordance with an embodiment of the present invention.

In order to study more complex subcellular structures, WDT was used to image human colon adenocarcinoma cells (HT29), using a 63×/1.4 NA oil immersion objective. The z-stack consisting of 140 frames was acquired in 150 nm z-steps. The results obtained on a cell that has recently divided are summarized in FIG. 6 which shows a false-coloured 3D image of an HT-29 cell, where sub-cellular structures are clearly observed: cell membrane in blue, nuclei in green, and nucleoli in red. These areas are first chosen by thresholding based on the phase values (0.6 rad for nucleoli and 0.1 rad for membrane) and then detailed based on morphology.

In preferred embodiments of the present invention, the disclosed methods for tomographic quantitative phase imaging of transparent structures using white light diffraction phase microscopy may be implemented as a computer program product for use with a computer system. Such implementations may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A method for obtaining a tomographic phase image of a specimen, the method comprising:
   a. illuminating the specimen with substantially temporally incoherent light through an objective of high-numerical aperture, the temporally incoherent light characterized by a focus;
   b. stepping the focus of the temporally incoherent light to a sequence of successive focal planes within the specimen;
   c. forming a scattered phase image of the specimen in an image plane where the scattered phase image of the specimen corresponds to each of the successive focal planes;
   d. solving for the scattered field in wavevector space;
   e. deconvolving a derived instrument function to obtain specimen susceptibility in wavevector space; and
   f. transforming the specimen susceptibility to derive a three-dimensional phase tomogram of the specimen.

2. A method in accordance with claim 1, wherein the specimen is substantially transparent in a visible portion of the electromagnetic spectrum.

3. A method in accordance with claim 1, wherein the specimen is opaque in a visible portion of the electromagnetic spectrum.

4. A method in accordance with claim 1, wherein the specimen is substantially transparent in an infrared portion of the electromagnetic spectrum.

5. A method in accordance with claim 1, wherein forming a scattered phase image of the specimen in an image plane corresponds to measuring a temporal cross-correlation function between a scattered field and a reference plane wave.

6. A method in accordance with claim 5, wherein the reference plane wave traverses the specimen.

7. A method in accordance with claim 1, wherein the specimen is a biological cell.

8. A method in accordance with claim 1, wherein forming a scattered phase image includes combining a plurality of interferograms obtained with distinct phase retardation rings.

9. A method in accordance with claim 1, wherein forming a phase image includes obtaining a single interferogram from an off-axis type interferometer.

10. A method in accordance with claim 9, wherein the off-axis type interferometer is a diffraction phase microscope.

* * * * *